United States Patent [19]

Ramel et al.

[11] Patent Number: 4,959,324
[45] Date of Patent: Sep. 25, 1990

[54] SAMPLE PAD ASSAY INITIATION DEVICE AND METHOD OF MAKING

[75] Inventors: Urs A. Ramel, Portola Valley; Michael P. Allen, Sunnyvale; Prithipal Singh, Los Alto Hills, all of Calif.

[73] Assignee: ChemTrak, Inc., Sunnyvale, Calif.

[21] Appl. No.: 353,910

[22] Filed: May 18, 1989

Related U.S. Application Data

[63] Continuation-in-part of Ser. No. 324,407, Mar. 16, 1989, which is a continuation-in-part of Ser. No. 195,881, May 19, 1988, and Ser. No. 64,883, Jun. 22, 1987.

[51] Int. Cl.$^5$ ............... G01N 21/79; G01N 31/22; C12Q 1/54; C12Q 1/60
[52] U.S. Cl. ............................. 436/169; 436/170; 422/56; 422/57; 422/58; 422/61; 435/11; 435/14; 435/810
[58] Field of Search ............... 436/169, 170; 422/58, 422/57, 56, 61; 435/810, 11, 14

[56] References Cited

U.S. PATENT DOCUMENTS

| | | |
|---|---|---|
| 4,477,575 | 10/1984 | Vogel et al. . |
| 4,647,541 | 3/1987 | Guadagno et al. .............. 422/56 |
| 4,774,192 | 9/1988 | Terminiello et al. . |
| 4,780,280 | 10/1988 | Berger et al. .................. 422/56 |

FOREIGN PATENT DOCUMENTS

| | | |
|---|---|---|
| 0191640 | 8/1986 | European Pat. Off. ............ 436/169 |
| 0286371 | 10/1988 | European Pat. Off. . |
| 2222951 | 7/1974 | Fed. Rep. of Germany . |
| 2201241 | 8/1988 | United Kingdom ............... 422/56 |

*Primary Examiner*—Robert J. Warden
*Assistant Examiner*—Thalia P. Vassilatos
*Attorney, Agent, or Firm*—Bertram I. Rowland

[57] ABSTRACT

A self-contained assay device is provided, where an analyte may be detected or be quantitated by measuring the distance of a detectable signal from a predetermined site. The device employs two strips separated by a gap, where a flow path is completed by movement of a sample receiving pad into the gap. The movement of the sample receiving pad also results in release of a reagent solution which is then transported through the pad into the quantitation area where the amount of analyte may be determined. Various chemistries may be employed for providing a detectable signal.

19 Claims, 4 Drawing Sheets

SAMPLE PAD ASSAY INITIATION DEVICE AND METHOD OF MAKINGr

CROSS-REFERENCE TO RELATED APPLICATIONS

This application is a continuation-in-part of application Ser. No. 324,407, filed Mar. 16, 1989, which is a continuation-in-part of application Ser. Nos. 195,881, filed May 19, 1988 and 064,883, filed June 2, 1987, which disclosures are incorporated herein by reference in their entirety.

INTRODUCTION

1. Technical Field

The field of the subject invention concerns diagnostic assay strips permitting visual measurement from any fluid and providing for red blood cell free fluid from blood.

2. Background

The ability to measure a wide variety of physiologically active compounds, both naturally occurring and synthetic, has become of increasing importance, both as an adjunct to diagnosis and therapy. While for the most part, assays of physiological fluids and drugs have required clinical laboratory determinations, there is an increasing awareness of the importance of being able to carry out assay determinations in the doctor's office and in the home. To be able to perform an assay in a doctor's office or home requires that an assay have a simple protocol and be relatively free of sensitivity to small changes in the conditions under which the assay is carried out. Importantly, inaccurate measurements of reagents and sample should whenever feasible be avoided. Numerous systems have been developed in efforts to try to address the various problems associated with analysis outside of the clinical laboratory. There is, nevertheless, a continuing interest in providing improved and alternative methods to those which are presently generally available.

Exemplary of this situation is the need today to be able to determine cholesterol levels or low or high density lipoprotein levels in blood. There is a clearly established relationship between total blood cholesterol (mainly LDL fraction) and coronary artery disease (Journal of the American Medical Association (1985) 253:2080–2086). New guidelines have been established for adults over 20 years of age to identify risk groups associated with blood cholesterol level. These levels are as follows: <200 mg/dl is a desirable blood cholesterol; 239 mg/dl is borderline high blood cholesterol; >240 mg/dl is high blood cholesterol.

Cholesterol levels can be controlled by both diet and cholesterol lowering drugs. The key is to identify those individuals at risk. Being able to monitor one's own cholesterol at home for those individuals at risk will provide a significant tool in monitoring cholesterol levels and reducing the potential for heart disease. The measuring of other naturally occurring compounds of physiologic importance and synthetic drugs is also of great interest. For example, therapeutic dosage monitoring, drugs of abuse, iodothyronines, alcohol, cytokines, as well as numerous other haptens and antigens are monitored. Also of interest are microorganisms β-HCG for ectopic births, antibodies associated with disease, and the like.

In many of the assays it will be necessary to provide a blood sample free of red blood cells to a measurement strip. Furthermore, for home use or use by non-technical individuals, it will be desirable that the volume of sample applied to a measurement strip permit a relatively broad range of sample volume, which is then accurately metered to the measuring strip. Any such device must be relatively simple, provide reproducible results, and be in a form which allows it to be joined to a measurement strip in a fixed or removable manner.

RELEVANT LITERATURE

Demacker, et al., Clin. Chem. (1983) 29:1916–1922 reports the evaluation of cholesterol assay kits. Studies associated with enzyme assays include Gochman and Schmitz, Clin. Chem. (1971) 17:12; Paul, The Enzymes (1963) 8:227–274; Current Status of Blood Cholesterol Measurement in Clinical Laboratories in the United States: A Report from the Laboratory Standardization Panel of the National Cholesterol Education Program (1988) 34(1):193–201; and U.S. Pat. Nos. 4,391,904; 4,366,241; 4,168,146; 4,435,504; 4,533,629; 4,540,659, and references cited therein. See also, Zuk, et al., Clin. Chem. (1985) 31:1144.

German Patent No. 22 22 951 describes a filter assembly containing chemical reagents for removing cells from blood and measuring CPK.

SUMMARY OF THE INVENTION

Methods and devices are provided, where the devices employ a continuous flow path having at least three regions, a fluid transport region, a sample region, a measuring region and optionally a mixing region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. By appropriate choice of reagents, the height of a signal can be related to the amount of analyte in a sample.

BRIEF DESCRIPTION OF THE DRAWINGS

FIG. 2b is a diagrammatic plan view of a cover plate which is situated over the intermediate plate of FIG. 2a;

FIG. 4 is an alternative design of the subject device with;

DESCRIPTION OF SPECIFIC EMBODIMENTS

Methods and apparatus are provided for the measurement of an analyte employing a continuous flow path, which has a sample receiving region as an internal region, which is brought into contact with the adjacent two regions to serve as a bridge. Prior to the addition of sample to the sample receiving region, the sample receiving region is inhibited from transport of fluid to complete the path. After receiving sample, the sample receiving region acts as a bridge between first and second portions of the path, where the first portion serves to transport fluid to the sample receiving region and the second portion is the measuring region, optionally joined to the sample receiving region by a mixing region.

Various techniques may be employed for organizing the flow path, inhibiting transport by the sample region, and providing for flow of a reagent solution through the sample region into the measuring region. In addition, various chemistries may be employed, using different types of reagent systems to produce the desired signal. The assay may be qualitative or quantitative. With agglutination assays, qualitative results may be obtained. For quantitative, the extent of the border of the signal from the sample region indicates the amount of analyte in the sample.

The flow path is primarily divided into three parts. The first part is a bilbulous short element which serves by capillary action to wick or transport reagent solution to the sample receiving element. For the most part, the transport element will be a bibulous strip which absorbs a hydrophilic liquid and allows for transport of the reagents contained in the reagent solution, without chromatographing the components of the reagent solution.

The sample receiving element serves a plurality of functions. The sample receiving element receives a sample and may, for the most part, have one or more members of a signal producing system present on the sample. Generally, the members will be nondiffusively bound, so as to be retained on the sample receiving element, although in other situations, diffusively bound members of the signal producing system may be present. The sample receiving element also serves as a bridge for transferring the reagent solution through the sample receiving element to the measuring element. For the most part, prior to the time that the transport element serves to transport reagent solution to the sample receiving element, the sample receiving element will be inhibited from acting as a bridging element between the transport element and the measuring element. After receiving the sample, the sample element is then permitted to be a bridging element which allows for the flow of the reagent solution through the sample element and into the measuring element.

The measuring element will be an extended member, which allows for flow of the reagent solution through the measuring element, by means of capillary action. The measuring element will have one or more members of the signal producing system present on the measuring element, where the height or distance of the signal board, the distance from the sample receiving element to the signal front, will be related to the amount of analyte in the sample and on the sample receiving member. Alternately, appearance of a signal at a predetermined area can indicate the presence or absence of an analyte. Gold sol assays are illustrative.

By appropriate choice of members of the signal producing system for a quantitative assay, visually observable color fronts may be obtained, fluorescent signals, or the like. In addition, the measuring element may have one or more additional regions between the measuring region, and the sample receiving element. These regions may serve to control the dynamic range of the assay, to provide a delay before the elements of the signal producing system move into the measuring region to allow mixing or a reaction to occur, and the like. By providing for a reaction in this region with a member of the signal producing system, the dynamic range of the assay will be changed in the measuring gene. Since for many analytes there may be a threshold value which is of interest and values below the threshold are not of interest, one could provide a sufficient amount of reagent in a threshold contact region to react with a member of the signal producing member, so that the threshold value becomes the zero or low value observed in the measuring zone. The reaction may be as a result of specific binding pair member complex formation, chemical reactions involving transformation of a chemical reactant to a product, or the like. The mixing region will usually be a bibulous member which serves to transport the liquid medium from the sample receiving element to the measuring zone or threshold zone.

Various techniques may be employed for inhibiting fluid flow to and from the sample receiving element to the other elements involved in the flow path. Of particular interest is the use of a slide which can be moved from a first position, where the sample receiving element receives the sample, to a second position where the sample receiving element serves as a bridge between the two other elements of the flow path. The slide therefore prevents sample spreading to the other elements of the flow path, before it is time to carry out the assay. The path of the sample receiving element, in moving from the site at which the sample is received to the site where it is in the flow path, may provide for means for removing excess sample from the sample receiving element. Such means provides for a quantitative measure of the amount of sample received by the sample receiving element. Thus, by having a region in the path of the slide which is narrowed, so as to remove unabsorbed sample medium, without significantly squeezing the sample receiving element, the amount of sample absorbed by the sample receiving element can be relatively accurately reproduced. The narrowing may be as a result of a convexity, such as a rod in relief, a roller, or any convenient scraping means. The narrowing of the path should provide a space about equal to or slightly less than the wet thickness of the sample receiving element. The slide, therefore, not only serves to move the sample receiving element, but also to meter the amount of fluid absorbed by the sample receiving element.

The slide may also serve an additional function in releasing the reagent solution. In providing for a self-contained device, it is desirable that the device include the reagent solution. In order to prevent evaporation, the reagent solution may be packaged in a sealed pouch situated in a well. The slide can be provided with an arm which scores the pouch, so as to open the pouch and release the fluid. By having one end of the transferring element in the well, the transferring element will transport the medium to the sample pad. Therefore, in moving the slide, one may move the sample receiving element, monitor the amount of fluid associated with the sample receiving element, as well as release the reagent solution for development of the assay.

The subject method may be employed in any situation where a fixed amount of a substance is involved, which can be transferred to the sample receiving element for measurement and ultimately an interaction occurs with another compound to produce a detectable boundary. These types of assays may be illustrated by ELISA assays, EMIT assays, sandwich assays, CEDIA assays, agglutination assays, or the like.

Depending upon the protocol, the sample receiving element to which the sample is added may be prepared in a variety of ways. It may be untreated, impregnated with buffer, or provide one or more reagents of a signal-producing system. A variety of sophisticated reagents, protocols or regimens can be devised based on a limited amount of material migrating to produce a boundary in proportion to the amount of analyte present. Examples of protocols would include particles having first and second ligands, where the first ligand competes with analyte for receptor bound to a surface. After carrying out the competition for a limited amount of receptor between analyte and particle, an aliquot of the assay medium is transferred to the sample receiving element and the particle transported with effluent through the measurement zone. By having receptor for the second ligand in the measurement zone, the particle boundary will be defined by the number of particles added to the pad. By having colored particles, charcoal particles, magnetic particles, particles coated with gold and selenium salts, dyes, dye-polymer conjugates, proteins with high visible extinction coefficients, e.g., phycobiliproteins, or the like, the boundary will be readily defined.

Any technique which allows for binding of a detectable entity in proportion to an analyte of interest may be employed. These may include cleavage of a bond to release the entity, where the bond to the entity is not cleavable when the entity is bound to a receptor, binding to a support which inhibits migration of the entity in proportion to the amount of analyte in a sample, or the like. The entity may be a particle as described above, an enzyme which catalyzes the production of a detectable product, or the like.

Of particular interest is where a product is produced on the sample receiving element which provides for a detectable boundary. For example, where the analyte is a substrate, the sample receiving element may be impregnated with the appropriate enzyme or enzymes to provide for a product. Normally, the enzyme product will react, either directly or indirectly, with a compound which is fixed in the assay measurement zone. This may be exemplified by cholesterol, glucose, or the like, which reacts with an oxidase to provide an oxidizing species. The oxidizing species may then react with the bound compound or a mobile compound which reacts with the bound compound, to produce a detectable boundary. Illustrative of this situation would be the hydrolysis of serum cholesterol ester by cholesterol esterase (EC:3.1.1.13) and subsequent oxidation of cholesterol by cholesterol oxidase (EC:1.1.3.6) to produce a stoichiometrically identical amount of $H_2O_2$. This $H_2O_2$ is formed at the sample receiving element and combines with horseradish peroxidase (HRP) which is in the mobile phase. The $HRP.H_2O_2$ reacts with a bound substrate to produce a detectable boundary.

Depending upon the assay, other reagents may also be present. For example, detergents find use where a lipophilic analyte in blood is involved, where the lipophilic analyte binds to proteins present in the blood. This may be illustrated by cholesterol which binds to proteins, as for example in very low, low, and high density lipoproteins. Thus, detergents such as non-ionic, anionic, or cationic detergents may be employed. Of particular interest are polyoxyalkylenes, ethoxylated alkylphenols, octylphenoxypolyethoxyethanol, octylphenol-ethylene oxide condensates and polyoxyethylene lauryl ethers, or anionic detergents, such as bile acids, e.g., sodium cholate and sodium taurocholate. In addition, various sticking agents or adhesives may be employed, such as gum arabic. Also of interest will be proteins which are substantially non-interfering, which may include gelatin, casein, serum albumin, or gamma globulins. In addition, the reagent pad may include preservatives, such as sucrose, polyvinyl alcohol, polyvinyl pyrrolidone, dextran or sodium azide. Finally, a buffered solution will normally be employed for impregnating the sample receiving element, where any convenient buffer may be employed, generally a substantially dilute buffer, which may include phosphate, tris, MOPS, borate, carbonate, or the like. Usually, the buffered solution will be at a pH in the range of about 4 to 9. The buffer concentration will generally be from about 10 to 500 mM.

In the case of the cholesterol assay as illustrative of other assays, the impregnating solution will have from about 2 to 100 units/ml of the two enzymes, cholesterol esterase and cholesterol oxidase. The detergents will be in total weight from about 0.1 to 5 weight percent of the medium, while in the case of mixtures the weight of the non-ionic detergents may be from about 10 to 90%, usually from about 25 to 75 weight percent of the total detergent mixture. The binding agents or adhesives will generally be in the range of about 0.2 to 10, more usually from about 1 to 5 weight percent of the medium. A preservative or hydrogen bonding agent may be present in from about 1 to 20 weight percent, more usually from about 2 to 10 weight percent. The remaining additives will generally be present in total amount of less than about 10 weight percent, more usually of less than about 5 weight percent. The remaining composition may be water, non-reactive ingredients, excipients, extenders, and the like.

In the case of thyroxine, various reagents may be used to release the polyiodothyronines from binding protein, e.g., thyroxine binding globulin. Illustrative reagents include sodium hydroxide, tetrachlorothyronine salicylate, 8-amino-1-naphthalenesulfonic acid, 2-hydroxy-4-methoxybenzophenone-5-sulfonic acid, etc. (see EPA No. 0 133 464).

Any analyte may be determined by using a variety of different protocols; for example, by employing conjugates of an epitopically cross-reactive compound and an enzyme such as horseradish peroxidase, where antianalyte receptors, particularly antibodies, are uniformly bound in the measurement zone. In addition, an oxidase is also uniformly bound in the measurement zone. The presence of analyte in the sample will provide for competition between analyte and enzyme conjugate for available antibody. The more analyte present, the further the limited amount of conjugate will progress. By employing as the reagent solution a reactant which in combination with the oxidase, which produces hydrogen peroxide, and a leuco dye, which forms a colored dye upon a horseradish peroxidase catalyzed reaction between hydrogen peroxide and the leuco dye, the color front will be related to the amount of analyte in the sample. For example, glucose oxidase may be used with glucose, urea oxidase with urea, and the like.

Different protocols may be used for different analytes. For theophylline, for example, the same reagents may be employed as described in Zuk, et al., supra. The measuring region has antitheophylline antibodies. The wicking solution comprises theophylline-HRP conjugate in PBS and glucose oxidase or the glucose oxidase may be in the measuring region. After wicking the sample, the measurement region may be flooded with substrate, e.g., 4-chloro-1-naphitrol and glucose in PBS.

For a thyroxine (T4) assay, the sample is contacted with a thyroxine releasing reagent, which may be present on the membranes for separating the red blood cells. The measurement region would comprise anti-T4 antibodies. The wicking solution and developer would be analogous to the theophylline assay, substituting theophylline with T4 in the conjugate. In the same way, other hapten analytes could be assayed.

The assay is carried out by impregnating a sample receiving element, usually a pad, which serves as a bridge between the other flow path elements positioned in tandem juxtaposition along their long axes. Thus the two elements define one long flow path, usually comprised of two differently sized bibulous strips with a separation between the two strips, where the sample receiving element may act as a bridge to allow for fluid flow between the two strips Where blood is the sample, the sample receiving element is positioned under a red blood cell removing filtering device. The blood sample will normally be one or a series of small drops, generally having a total volume under about 100 μL, more usually from about 10–50 μL. The layers through which the sample flows will usually include a mesh layer, a first membrane, and a second membrane cooperating with the first membrane to ensure the substantially complete removal of any interfering cells from the blood sample. The first cellular separation member is used to reduce the concentration of red and white blood cells received by the second filtration member. By lowering the red blood cell content from about 10 to 90%, usually from about 30 to 90% of the original red blood cell content, with the first membrane member, the second membrane member is able to efficiently and accurately remove at least substantially all of the red blood cells from the blood sample. Since the first membrane acts as a coarse separation means, the first membrane may take any of a wide variety of forms.

Various packings or sieving depth filters may be employed, such as glass fibers, cellulose filters treated with red blood cell capture reagents, glass fiber filters, or synthetic fiber filters. Glass fiber filters are available from such manufacturers as Whatman, Schleicher and Schuell, MSI, and Pall. The glass fiber filters are further characterized by a glass fiber diameter in the range of about $0.5-9\mu$, and a density of about 50 to 150 g/m². The glass fiber filters may be illustrated by S&S Glass 30, Whatman GFD, and S&S 3662.

Other coarse separation membranes may include cellulosic membranes, e.g. filter paper, to which red blood cell binding proteins or agglutination agents immobilized. Such proteins may include lectins, antibodies specific for RBC surface membrane proteins, thrombin, ion exchange agents, etc. The preparation of such filters by conjugating proteins or other agents to cellulose is well known. Cellulose may be activated in a wide variety of ways employing carbodiimide, carbonyl diimidazole, cyanogen bromide, chloroacetic acid, where the acid may then be activated with carbodiimide, or the like. The literature is replete with examples of binding of proteins to cellulosic membranes for a variety of reasons, which techniques may be employed here. Alternatively, multiple layers of coarse separation membranes may be employed.

With the two membranes, immediately beneath the first membrane will be the second membrane, which will be in fluid receiving relationship with the first membrane, either in contact with the first membrane or in close proximity thereto. Generally, the spacing between the first and second membranes will not exceed a distance which inhibits fluid flow, so that fluid readily flows from the first to the second membrane. The non-asymmetric membranes which are employed will be those in the medium porosity range, having an average porosity in the range of about $0.65\mu$ to $7\mu$, preferably about 1 to $5\mu$, where the pores may or may not be of substantially uniform diameter through the membrane. By contrast, where an asymmetric membrane is employed, that is, the diameter of the pores varies from one surface to the other, desirably the membrane will have a minimum porosity not less than about $0.4\mu$, preferably not less than about $0.45\mu$, and the maximum porosity will generally not exceed about $40\mu$, more usually not exceed about $20\mu$. Illustrative microporous membranes which may find use include Filterite polysulfone asymmetric, 20 $\mu$–$0.45\mu$, Sartorious cellulose acetate, $1.2\mu$, Nucleopore, etc.

The choice of the second membrane is important, since the amount of red blood cell lysis is dependent on a number of factors. Depending on the size of the pores, the amount of lysis will greatly vary. Since lysis results in release of colored cell components, which interfere with detection of the border in the measuring strip and act to decompose hydrogen peroxide, merely removing cells is insufficient. A further consideration is the pressure differential across the membranes. Again, the appropriate choice of membranes will affect the pressure drop and forces acting on the cells, where the pressure differential can affect the stability of the cells.

Thus, the two membranes serve to act together to efficiently and accurately remove red blood cells from the blood sample with little, if any, hemolysis, so as to provide a plasma or serum sample which may be accurately analyzed without interference from hemolytic products, such as heme.

The sample receiving element will be immediately beneath the red blood cell removing membranes and in fluid receiving relationship with the membranes. The sample receiving element will normally be a bibulous member able to absorb the fluid. Various bibulous materials may be used, such as cellulosic materials, e.g., paper, or the like. The sample receiving element will usually be of a size in the range of 5 to 50 mm² surface area and a thickness in the range of about 0.1 to 2 mm, having a volume capacity of from about 1 to 30 $\mu$l. The sample receiving element may be round, square, rectangular, quadrilateral or polygonal, depending on the manner in which it is to be used to act as a bridge for the other members of the flow path. For further characterization see application Ser. No. 195,881, filed May 19, 1988.

The assay is carried out by impregnating a sample receiving element which serves as a bridge between two bibulous members positioned in tandem juxtaposition along their long axes to define a flow path. Thus the two strips define one long strip with a separation between the two strips, where the sample receiving element can act as a bridge to allow fluid flow between the two strips. A first bibulous transfer member serves to receive the transport and reagent solution, which may or may not have reaction components, depending upon the assay. The first bibulous transfer member, transfers the fluid to the sample receiving element. The sample receiving element receives the transport and reagent fluid from the first bibulous transfer member and serves as a bridge to transfer the reagent fluid to the assay measurement region.

The sample is prevented from interacting with the two bibulous members when sample is transferred to the sample receiving element. Besides the slide mechanism, other separation means may be employed. These separation means will usually comprise an inert non-porous film, which blocks transfer from the sample receiving element to the bibulous members of the flow path. The amount of sample accepted by the sample receiving element and involved in the assay medium may be controlled by providing for transfer of fluid beyond the amount saturating the sample receiving element through a non-wetting screen into an absorbent layer. After addition of the sample to the sample receiving element, and an incubation of up to about 30 minutes, the porous non-wetting material and absorbent layer are removed, leaving the sample receiving element as the sole repository of sample for the assay. Where a wiping film is employed it will be removed upon saturation of the sample receiving element. (See application Ser. No. 324,407, filed Mar. 16, 1989.)

The entire flow path may have a length of about 25 to 200 mm, more usually from about 50 to 150 mm, preferably about 100 mm. About 25 to 90% of the length of the flow path will be the measurement region comprising the quantitation zone, optionally a mixing zone and/or a threshold value zone. The mixing and or threshold value zone will generally be from about 5 to 35% of the flow path. The strips which provide for flow of fluid to and from the sample receiving element may be of the same or different length and will generally be from about 5 to 25 mm, more usually about 10 to 20% each of the length of the flow path. The upstream strips may be part of the measurement region strip, or an independent entity. Alternatively, this strip may be used to control the threshold value. The sample receiving element will generally be from about 1 to 10%, more usually from about 2 to 8% of the length of the flow path; the longer the flow path, the larger the sample receiving element may normally be. The width of the strips may be varied widely, usually being at least about 2 mm and not more than about 10 mm, preferably from about 3 to 7 mm. The two strips will usually each overlap the reactant pad by at least about 0.2 mm and not more than about 2 mm, usually about 1 mm, being primarily a matter of convenience, so long as the two strips are not in direct fluid communication.

Any convenient material may be used for the various bibulous parts of the assay strips forming the flow path. Usually, the thickness of the bibulous components will be in the range of about 0.05 to 2.0 mm, more usually 0.15 to 0.75 mm. A wide variety of bibulous supports may be employed, particularly cellulosic supports, such as chromatography paper, silica on a support, alumina on a support, and polymeric membranes such as nitrocellulose and nylon. The characteristics of the bibulous material employed for the measurement region or zone include the need in many instances to covalently or irreversibly bind an indicator molecule to the support, that the color developed should be clear and sharp, and that the fluid should be capable of flowing at a convenient rate through the bibulous members.

Of particular interest is an assay device which is self-contained and only requires the sample for carrying out the assay. The device may serve as a one-step diagnostic test device using a disposable cassette format. The device may be fabricated of three individual injection molded parts into which various components of the assay system are associated. These include the filtration medium designed to separate plasma from whole blood, means for metering a precise sample volume, a slide to transfer the sample receiving element to the transfer and measurement elements and to release a transport and reagent solution. The transport solution initiates capillary migration through the flow path resulting in the development of a detectable boundary related to the amount of analyte in the sample.

Figure 1:
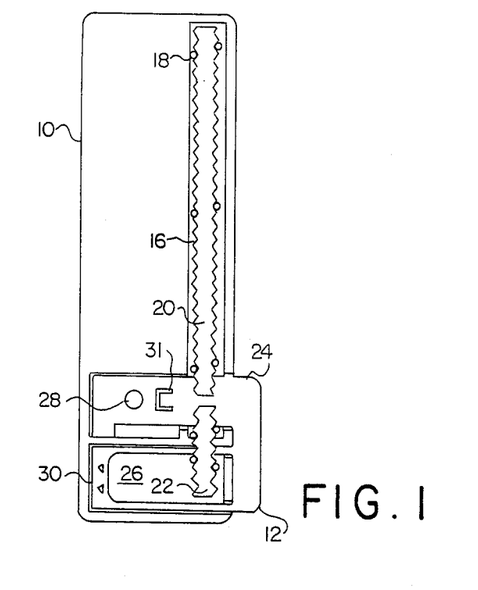
FIG. 1 is a diagrammatic plan view of the base plate and slide of a device according to the subject invention.
Figure 2A:
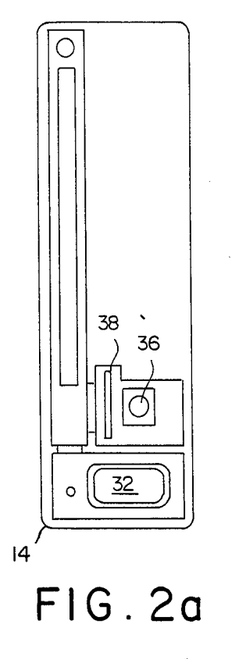
FIG. 2a is a diagrammatic plan view of an intermediate plate which covers the base plate.
Figure 2B:
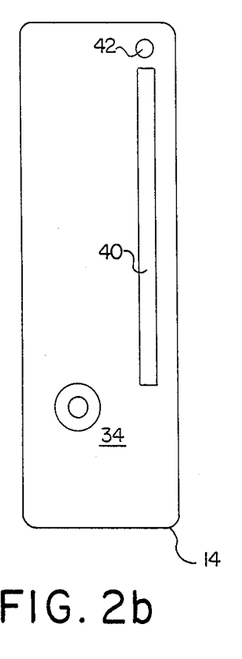

For further understanding of the subject invention, the drawings will now be considered. The invention may be fabricated from three injection molded parts or by any other convenient process. The parts comprise a base plate 10, a slide 12 and a cover plate 14, as shown in FIGS. 1 and 2. The base plate 10 consists of a cutout to accept the slide 12, a slot 16 with locating pins 18 into which the quantitation strip 20 and bibulous strip 22 are precisely positioned, maintaining about a 2 mm gap 24 between them, and a well 26 designed to capture the released transport solution, e.g., wicking buffer.

The slide 12 consist of a vented receptor site 28 into which the reagent pad is inserted, an arm 30 with dual shearing designed to facilitate the release of the transport solution from a pouch which is housed in well 32 of cover plate 14, and a snap 31 to lock the slide in place, once pulled. The cover plate 14 consists of a well 32, which houses a sealed foil pouch (not shown) containing the transport solution. The cover plate has an orifice 34 for the introduction of the sample. Underneath orifice 34 are filters 36, for separating cells from blood samples. The filtration system may comprise dual glass fiber disks and a final filtration membrane in order to deliver cell free plasma to the sample receiving element. The cover plate also comprises the squeegee metering bar 38, which serves to control the volume of sample absorbed by the sample receiving element, as well as a viewing slot 40. At the top of the viewing slot 40 is an indicator hole 42, which changes color when the test is complete to inform the user that a reading may be taken.

Figure 3A:
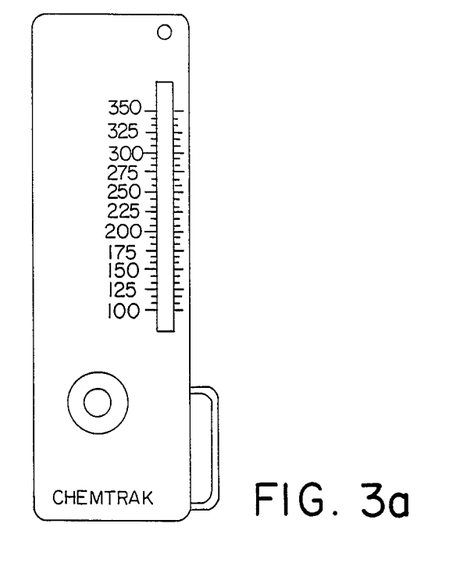
FIG. 3a is a plan view of an assembled device.

The final assembly is depicted in FIG. 3, where the assembled device is obtained by introducing the slide 12 into base plate 10, positioning transfer strip 22 and measurement strip 20 at their appropriate sites, introducing the transport solution pouch into well 32, assembling the cover plate and base plate and then sealing, conveniently by sonic welding, the base plate and the cover plate. This procedure locates the sample receiving site of the slide directly beneath the filtration media of the cover plate, as well as locating the shearing points of the slide beneath the foiled sealed pouch located in the cover plate.

A modified device is shown in FIG. 4, where an additional liquid reagent is supplied for flooding the measurement strip.

Figure 4A:
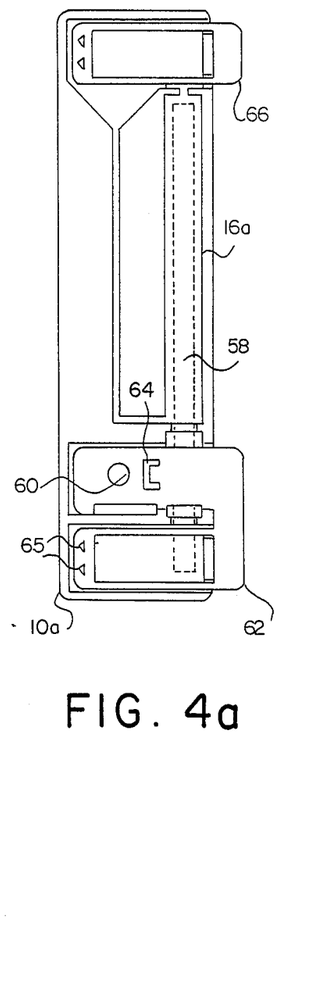
FIG. 4a being a diagrammatic plan view of the base plate and slide.
Figure 4B:
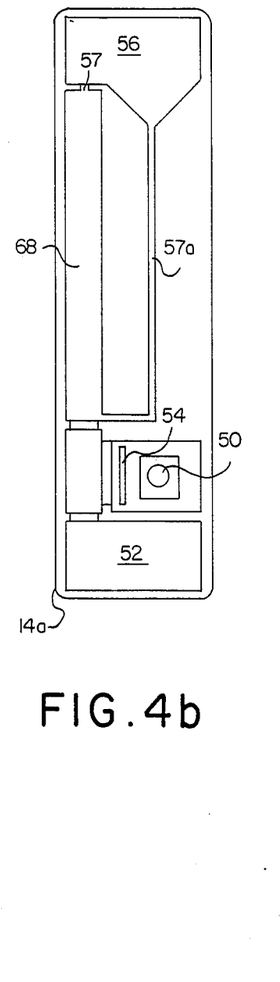
FIG. 4b being a diagrammatic plan view of the cover plate.

The device comprises a base plate 10a and a cover plate 14a, as well as slide 62. The sample is introduced at sample receiving site 50. Cover plate 14a comprises well 52 which may include one or more pouches with the same or different reagent solutions. Also involved with the movement of the slide is squeegee 54, which serves to control the volume absorbed by the sample receiving element.

Additional to the subject device is a developer pouch well 56 which houses a pouch which has a reagent solution for developing the detectable signal. When the reagent is released from the pouch, the reagent may enter slot 16a through channels 57 and 57a, so as to flood the slot and substantially wet the measurement strip 58. The slide 62 includes the sample receiving element 60 as well as slide snaplock 64 and dual shearing points 65 for shearing the pouch housed in well 52. A second slide 66 serves to open the pouch in well 56 to release the developer solution. A viewing window 68 is superimposed over slot 16a, so as to view measurement strip 58.

In order to carry out a cholesterol measurement, the user lances his or her finger and applies a hanging drop of blood to the application site, which is a white central well with a red border. When the white center is no longer visible, a sufficient amount of blood has been applied. The user then waits about 30 seconds to 2 min or more to allow adequate filtration and recovery of plasma onto the sample receiving pad. Impregnated on the sample receiving pad is are cholesterol esterase, cholesterol oxidase and detergents in sufficient amount to reaction with all of the cholesterol ester and cholesterol and to disperse the cholesterol. The slide is then pulled until it snaps into place. At this point the reagent pad containing the plasma sample has been metered by the squeegee metering bar and is brought into contact and fluid transferring relationship with the transfer strip and the measurement strip over the two mm gap. The shearing points of the slide have also pierced the foil seal of the pouch in the well of the cover plate, releasing the transport solution into the receiving well in the base plate. The transport solution is 0.1-2 ml of an aqueous buffer which may contain horseradish peroxidase in sufficient amount to insure rapid reaction of the hydrogen peroxide and dye. This begins the wicking of the strip assembly which washes the plasma sample from the sample receiving element onto the measurement strip. The measurement strip is impregnated with a peroxidase substrate, particularly a modified N, N-dimethylaniline. (See application Ser. No. 195,881, filed May 19, 1988.) The reaction of the reagents results in a colored region with a defined boundary, thereby giving the user a precise reading of the cholesterol level. This reading is made when the color indicator site above the viewing slot shows the test is complete. Normally, it will take about 15 min for the assay to be complete, reading the peak of a blue area in the viewing slot.

Therapeutic dosage monitoring assays may be performed in accordance with the subject invention employing commercially available devices. The immunochromatographic strip from a theophylline Acculevel ® device was removed from the plastic cassette. The strip was affixed to a 10 mil acetate plastic backing with 3M 415 double stick adhesive tape so that the dye band on top of the strip faced upwards and the top of the strip was flush with the end of the plastic backing. At the lower end of the strip, an 11×5 mm section of S&S 470 paper to serve as a mixing zone was positioned on the backing to provide a 1 mm overlap with the bottom of the strip and a 1 mm overlap with a 7×5 mm section of Whatman 31ET paper also adhered to the backing to serve as a sample site. An additional 11×5 mm section of S&S 470 paper was adhered below the 31ET paper with a 1 mm overlap to the 31ET paper and ending at the terminus of the plastic backing. To interrupt wicking between the 31ET paper and the two 470 sections, 3×10 mm pieces of Mylar were positioned between the 1 mm overlap points (The Acculevel ® control solution was diluted 1:10 with pH 7.0 phosphate buffer. Solutions of 0.5 μg/mL and 1.0 μg/mL theophylline in phosphate buffer were gravimetrically prepared. The samples were applied to the 31ET paper section of the strip with a micropipet. In all cases, 10 μl of sample was applied. After application of the sample, the Mylar pieces were removed and the strips placed in the Acculevel ® wicking buffer (solution 1) with the lower 470 section dipped in the solution. The solution wicked through the lower 470 section, through the 31ET paper (sample site), through the mixing zone, and finally through the immunochromatographic strip. The wicking was allowed to continue until the dye level at the top of the strip smeared.

Immediately after completion of the wicking, the strip was removed from the wicking solution and the immunochromatographic paper was immersed in Acculevel ® developer (solution 2). A color band of good quality and rocket front developed over several minutes. When the color development was complete, the strip was removed from the developer and the migration height of the color band was measured from the bottom of the strip to the color band front (apex).

| RESULTS | MIGRATION HEIGHT |
|---|---|
| 1/10 Acculevel ® control 2.90 μg/ml | 39 mm |
| .5 μg/mL theophylline solution | 33 mm |
| 1.0 μg/mL theophylline solution | 40 mm |

Creating a 2-point curve with the 0.5 and 1.0 μg/mL solutions allowed for interpolation of the 1:10 Acculevel ® control. A value of 0.9 μg/mL was indicated. This value falls within the control range 0.83–1.23 μg/ml.

In some instances, the sample receiving element may include reagents which react with the analyte. If insufficient time for reaction is provided by the time the transport solution reaches the sample receiving element, then an incubation period of from 1 to 30 min. may be employed before the slide is moved to bring the sample receiving element into position in the flow path.

It is evident from the above results, that a simple self-contained device is provided which can be used without any technical experience. The user only requires the need of placing a sample at the appropriate position and then moving one or more slides at appropriate times. Reading can be done visually, although the reading may also be done by instrumentation if desired. Thus, a wide variety of analytes may be determined by untrained individuals in various settings, where a quantitative result can be obtained.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An analyte measuring device which cooperates with a signal producing system for producing a detectable signal in a detection zone, said device comprising:
a housing comprising a well adjacent to one end of said housing, a flow path for holding in position two bibulous strips spaced apart in tandem relationship to define a space, and proximal to said well an space for receiving a slide mechanism;

an orifice for receiving a sample displaced from and substantially aligned with the space between said two bibulous strips;

a slide element in said interspace comprising: (1) a sample receiving element positioned (i.) under said orifice when said slide element is in a first position, and (ii.) positioned in said space, when said slide is in a second position; and means for releasing a liquid into said well when said slide is moved from said first position to said second position; and first and second bibulous strips in said flow path, said first strip extending from said well to said space to transport liquid from said well to said sample receiving element and said second strip comprising said detection zone and extending from said space toward the end opposite from said well.

2. A device according to claim 1, wherein said device further comprises filter means situated in said orifice.

3. A device according to claim 1, further comprising means for removing excess sample from said sample receiving element as said sample receiving element moves from said first position to said second position.

4. A device according to claim 1, wherein said sample receiving element comprises as a member of said signal producing system, an enzyme which reacts with said analyte.

5. A device according to claim 4, wherein said enzyme is an oxidase.

6. A device according to claim 1, wherein said second bibulous strip comprises in the direction of flow, a first region comprising a first reagent which reacts with a member of said signal producing system to define a threshold value and a second region which comprises a second reagent which produces a detectable signal.

7. An analyte measuring device which cooperates with a signal producing system for producing a detectable signal as a detectable border, said device comprising:

a housing comprising a well adjacent to one end of said housing, a flow path for holding in position two bibulous strips spaced apart in tandem relationship to define a space, and proximal to said well an space for receiving a slide mechanism;

an orifice for receiving a sample displaced from and substantially aligned with the space between said two bibulous strips;

a slide element in said interspace comprising: (1) a sample receiving element positioned (i.) under said orifice when said slide element is in a first position, and (ii.) positioned in said space, when said slide is in a second position, said sample receiving element comprising a member of said signal producing system non-diffusively bound; and means for opening a pouch when said slide is moved from said first position to said second position;

means for removing excess sample from said sample receiving element as said sample receiving element moves from said first position to said second position: and first and second bibulous strips in said flow path, said first strip extending from said well to said space to transport liquid from said well to said sample receiving element and said second strip extending from said space toward the end opposite from said well comprising a measuring region in which a member of said signal producing system is nondiffusibly bound.

8. A device according to claim 7, wherein said removing excess sample means is a projection above said slide which contacts said sample receiving means as it moves from said first position to said second position.

9. A device according to claim 8, wherein said sample receiving means comprises a first member of said signal producing means non-diffusibly bound and said second bibulous strip comprises a second member of said signal producing means non-diffusibly bound.

10. A device according to claim 9, wherein said first member is an oxidase and said second member is a peroxidase.

11. A device according to claim 10, wherein said oxidase is cholesterol oxidase and said peroxidase is horse radish peroxidase.

12. A device according to claim 10, wherein said oxidase is glucose oxidase and said peroxidase is horse radish peroxidase.

13. A device according to claim 10, wherein said oxidase is alcohol oxidase and said peroxidase is horse radish peroxidase.

14. A device according to claim 7, wherein said second bibulous strip comprises in the direction of flow, a first region comprising a first reagent which reacts with a member of said signal producing system to define a threshold value and a second region which comprises a second reagent which produces a detectable signal.

15. A device according to claim 14, further comprising a second well situated proximal to the end opposite from said first well, at least one conduit from said well to the measuring region portion of said flow path for flooding said measuring region with a liquid; and means for releasing said liquid from said well into said flow path.

16. A device according to claim 7, further comprising a second well situated proximal to the end opposite from said first well, at least one conduit from said well to the measuring region portion of said flow path for flooding said measuring region with a liquid; and means for releasing said liquid from said well into said flow path.

17. A device according to claim 16, wherein said well houses a pouch containing said liquid; and said liquid releasing means comprises a slide situated in a interspace above said second well with a scoring arm for tearing said pouch.

18. A device according to claim 7, fabricated from a base plate and a cover plate welded together defining said space for said slide, said base plate comprising said flow path and said cover plate comprising said first well and orifice.

19. A method for detecting the presence of an analyte in a sample employing a signal producing system having a plurality of reagents being distributed between being bound non-diffusibly to a surface or free in solution, said signal producing system with said analyte producing a detectable signal in a detection zone on a measuring strip employed as a said surface, said method comprising:

applying said sample to a sample receiving element capable of moving from a first position to a second position, said second position in liquid transferring relationship with said measuring strip;

moving said sample receiving element to said second position;

transporting fluid to said sample receiving element for transporting at least one member of said signal producing system from said sample receiving element to said measuring strip; and allowing said fluid to wick through said measuring strip with formation of a detectable boundary at a distance from said sample receiving element in relation to the amount of analyte in said sample.

* * * * *

UNITED STATES PATENT AND TRADEMARK OFFICE
CERTIFICATE OF CORRECTION

PATENT NO. : 4,959,324
DATED : September 25, 1990
INVENTOR(S) : URS A. RAMEL, MICHAEL P. ALLEN & PRITHIPAL SINGH It is certified that error appears in the above-indentified patent and that said Letters Patent is hereby corrected as shown below:

At Col. 2, lines 47-50, delete:
"FIG. 2a is a diagrammatic plan view of an intermediate plate which covers the base plate;

FIG. 2b is a diagrammatic plan view of a cover plate which is situated over the intermediate plate of FIG. 2a;"

and insert:

--FIG. 2a is a diagrammatic top view of the cover plate which covers the base plate;

FIG. 2b is a diagrammatic bottom view of the cover plate shown in FIG. 2a.--

Signed and Sealed this

Thirteenth Day of June, 1995

Attest:

BRUCE LEHMAN

*Attesting Officer*        *Commissioner of Patents and Trademarks*